United States Patent [19]

Izumisawa et al.

[11] Patent Number: 5,420,344
[45] Date of Patent: May 30, 1995

[54] PROCESS FOR PRODUCING HIGHLY PURE TEREPHTHALIC ACID

[75] Inventors: Yoshiaki Izumisawa, Kitakyushu; Tsukasa Kawahara, Mizumaki; Yoshiyuki Sumi, Kitakyushu; Takehiko Baba, Kitakyushu; Yoshio Ishinaga, Kitakyushu; Katsuhiko Fukui, Kitakyushu; Hironori Ohgi, Kitakyushu, all of Japan

[73] Assignee: Mitsubishi Chemical Corporation, Tokyo, Japan

[21] Appl. No.: 134,907

[22] Filed: Oct. 13, 1993

[30] Foreign Application Priority Data

Oct. 13, 1992 [JP] Japan .................................. 4-274571
Apr. 19, 1993 [JP] Japan .................................. 5-091552

[51] Int. Cl.$^6$ ............................................. C07C 51/42
[52] U.S. Cl. ..................... 562/485; 562/412; 562/417
[58] Field of Search .............................. 562/485, 417

[56] References Cited

U.S. PATENT DOCUMENTS 3,584,039  6/1971  Meyer .
3,639,465  2/1972  Olsen et al. .
4,877,900 10/1989  Tamaru et al. .
4,892,972  1/1990  Schroeder et al. ................. 562/485

Primary Examiner—José G. Dees
Assistant Examiner—Dwayne C. Jones
Attorney, Agent, or Firm—Oblon, Spivak, McClelland, Maier & Neustadt

[57] ABSTRACT

A process for producing highly pure terephthalic acid, which comprises heating and dissolving crude terephthalic acid in water, and purifying it by contacting the aqueous solution with hydrogen at a temperature of from 260° to 320° C. in the presence of a platinum group metal catalyst, wherein the purification is initiated within three minutes after the aqueous solution under heating reaches a temperature of 250° C.

13 Claims, 2 Drawing Sheets

PROCESS FOR PRODUCING HIGHLY PURE TEREPHTHALIC ACID

BACKGROUND OF THE INVENTION

1. Field of the Invention

The present invention relates to a process for producing highly pure terephthalic acid. Particularly, it relates to a process for producing highly pure terephthalic acid by suppressing formation of impurities at the time of purifying crude terephthalic acid obtained by an oxidation reaction of p-xylene, by contacting it with hydrogen in the presence of a platinum group metal.

2. Discussion of the Background

Crude terephthalic acid obtained by oxidation of p-xylene usually contains relatively large amounts of various impurities including 4-carboxybenzaldehyde (hereinafter referred to simply as "4CBA"). Heretofore, it has been common that such terephthalic acid is purified and then used as a starting material for polyester.

As a purification method for such crude terephthalic acid, a method of subjecting the crude terephthalic acid to hydrogenation treatment or oxidation treatment has been known. As a method of subjecting crude terephthalic acid to hydrogenation treatment, a method has been proposed wherein an aqueous solution of crude terephthalic acid is subjected to hydrogenation reduction treatment at a high temperature under high pressure in the presence of a hydrogenation catalyst, and crystals of terephthalic acid are recovered from the treated aqueous solution (Japanese Examined Patent Publication No. 16860/1966).

By such a method of purifying crude terephthalic acid by hydrogenation, it is possible to remarkably reduce metal ions as inorganic impurities in the crude terephthalic acid and the amount of 4CBA which constitutes the largest content among organic impurities. However, by this method, it is impossible to completely remove organic impurities having unknown structures (hereinafter referred to as "coloring impurities") other than 4CBA, and part of such coloring impurities will remain in the purified terephthalic acid and will bring about, for example, coloring during the production of polyester, whereby whiteness of the polymer tends to deteriorate.

SUMMARY OF THE INVENTION

The present invention has been made to solve the above-mentioned problem in the conventional method for producing highly pure terephthalic acid. It is an object of the present invention to provide a process for producing purified terephthalic acid having a high purity by suppressing formation of coloring impurities at a high temperature prior to the purification by hydrogenation reduction by a method of purifying crude terephthalic acid by contacting an aqueous solution of the crude terephthalic acid with hydrogen at a high temperature under high pressure i.e. by a purification method by hydrogenation reduction.

In view of the above object, the present inventors have conducted extensive studies and as a result, have found that by limiting the time for exposure of crude terephthalic acid to a high temperature prior to the purification by hydrogenation reduction, particularly the time for exposure to a temperature of 250° C. or higher, it is possible to suppress formation of coloring impurities and thus to obtain purified terephthalic acid having an extremely high purity. The present invention has been accomplished on the basis of this discovery.

Thus, the present invention provides a process for producing highly pure terephthalic acid, which comprises heating and dissolving crude terephthalic acid obtained by an oxidation reaction of p-xylene, in water, and purifying it by contacting the aqueous solution with hydrogen at a temperature of from 260° to 320° C. in the presence of a platinum group metal catalyst, wherein the purification is initiated within three minutes after the aqueous solution under heating reaches a temperature of 250° C.

On the other hand, when the time until the purification is initiated after the aqueous solution reaches a temperature of 250° C., is shortened, dissolution may sometimes be inadequate depending upon the crystal particle size of the crude terephthalic acid, whereby if undissolved terephthalic acid crystals are supplied to the packed layer of a platinum group metal catalyst, a constant continuous operation will be impossible.

As a method for completely dissolving crude terephthalic acid, it has been common to provide a separate buffer dissolving vessel between a tubular type heater and a reactor composed of a packed layer of catalyst to completely dissolve crude terephthalic acid in the vessel (e.g. Japanese Examined Patent Publication No. 32618/1976).

However, the retention time in this buffer dissolving vessel is from a few minutes to a few tens minutes. Therefore, this method is not suitable for a process wherein the time until the purification is initiated after the aqueous solution reaches a temperature of 250° C., is limited within three minutes.

Under these circumstances, as a method for certainly dissolving crude terephthalic acid in a short period of time without using a buffer dissolving vessel and limiting the time until the initiation of purification after the temperature reaches 250° C., to a level within three minutes, the present inventors have invented a method of using a packed tower type reactor which has, at an upper inlet portion, a retention zone partitioned by an overflow wall and a catalyst layer located below the retention zone, wherein an aqueous solution of crude terephthalic acid is supplied to the retention zone and permitted to overflow over the overflow wall and then permitted to flow through the catalyst layer.

Now, the present invention will be described in detail.

BRIEF DESCRIPTION OF THE DRAWINGS

In the accompanying drawings.

BRIEF DESCRIPTION OF THE PREFERRED EMBODIMENTS

Figure 1:
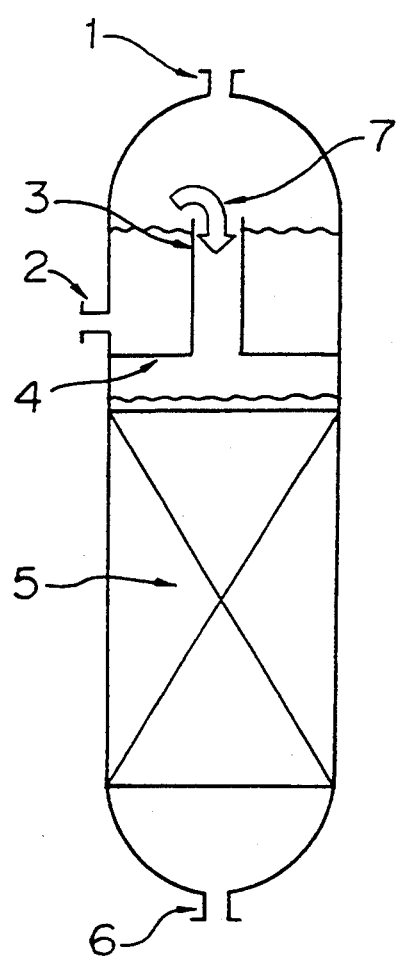
FIG. 1 is a view illustrating the structure of one embodiment of the packed type reactor to be used in the present invention.

The oxidation reaction of p-xylene is conducted usually by liquid phase oxidation with molecular oxygen in a solvent composed of a lower aliphatic carboxylic acid, particularly in an acetic acid solvent, in the presence of a transition metal compound and a bromine compound as a catalyst. The transition metal compound as a catalyst, may, for example, be a bromide, a benzoate, a naphthenate, a carboxylate such as acetate or an acetylacetonate of a transition metal such as manganese, cobalt, iron, nickel or chromium. The bromine compound may, for example, be a bromide of e.g. manganese, cobalt, iron, nickel or chromium, hydrobromic acid, sodium bromide, dibromoethylene, or tetrabromoethane. The bromide of a transition metal may serve as both the transition metal compound component and the bromine compound component. The molecular oxygen may, for example, be pure oxygen, air, Or a mixture of pure oxygen with an inert gas.

More specifically, for example, in a case where p-xylene is subjected to liquid phase oxidation in acetic acid to produce terephthalic acid, the starting material p-xylene is used in an amount of from 1 to 50% by weight relative to the acetic acid solvent. When a cobalt compound or a manganese compound and a bromine compound are used as the catalyst, these compounds are used so that cobalt atoms will be from 10 to 5,000 ppm by weight, manganese atoms will be from 10 to 5,000 ppm by weight, and bromine atoms will be from 10 to 10,000 ppm by weight, relative to the solvent. Whereas, the molecular oxygen to be supplied to the oxidation reactor is used usually in such an amount that the oxygen will be from 3 to 20 mols per mol of p-xylene. The reaction is conducted usually at a reaction temperature of from 160° to 260° C. under a reaction pressure of from about 0.5 to 5 MPa (from 4 to 50 kg/cm$^2$G), and the retention time is usually within a range of from 10 to 200 minutes.

The crude terephthalic acid thus obtained usually contains from 50 to 10,000 ppm by weight of 4CBA as impurities, and is preferably purified by hydrogenation reduction, so that it can be used as a starting material for polyester. Namely, an aqueous slurry of crude terephthalic acid is heated to completely dissolve in water the crude terephthalic acid in the slurry, followed by contacting it with a platinum group metal in the presence of hydrogen at a high temperature under high pressure, whereupon purified terephthalic acid is obtained by crystallization.

More specifically, an aqueous slurry containing crude terephthalic acid usually in an amount of from 1 to 80 parts by weight, preferably from 15 to 65 parts by weight, per 100 parts by weight of water, is heated to dissolve the crude terephthalic acid in water, followed by a hydrogenation reaction at a temperature of from 260° to 320° C., preferably from 270° to 300° C. If the temperature exceeds 320° C., formation of by-products in the hydrogenation reduction reaction tends to be remarkable. On the other hand, if the temperature is lower than 250° C. the hydrogenation rate tends to be low. Using molecular hydrogen in an amount of from 0.05 to 10 Nm$^3$/hr, preferably from 0.1 to 3 Nm$^3$/hr, per 1 t/hr of the aqueous solution of crude terephthalic acid, the aqueous solution is contacted with the catalyst of a platinum group metal such as ruthenium, rhodium, palladium, platinum or osmium usually from 1 to 100 minutes. The total pressure of the reaction system here is usually from 5 to 15 MPa, preferably from 6 to 10 MPa, more preferably from 7 to 10 MPa. Such a platinum group metal catalyst is employed usually in a form supported on a carrier insoluble to the hot aqueous solution of terephthalic acid, such as active carbon. It is particularly preferred to employ a catalyst having from 0.1 to 10% by weight of palladium supported on active carbon (hereinafter referred to simply as "Pd/C") from the viewpoint of the purification effects. As the reactor, it is preferred to employ a packed tower type reactor.

Specifically, it is preferred that using a packed tower type reactor having Pd/C as a catalyst layer, the aqueous solution of crude terephthalic acid is passed through the catalyst layer in the presence of molecular hydrogen. The hot aqueous solution of terephthalic acid thus treated for purification, is then cooled to a level of from 70° to 180° C. to precipitate and separate terephthalic acid.

In the above described process for hydrogenation reduction, to supply an aqueous solution having crude terephthalic acid dissolved in water to the reactor, it is necessary to preliminarily heat the solution to a reaction temperature of from 260° to 320° C. If the solution is supplied to the reactor in such a state that non-dissolved particulate terephtharic acid still remains in the solution, not only it is impossible to accomplish hydrogenation purification, but also a trouble of clogging may result in the fixed bed of Pd/C, whereby the plant will have to be stopped. Therefore, heretofore, it has been common to ensure the dissolution by prolonging the retention time while maintaining the temperature at a level slightly higher than the dissolving temperature corresponding to the concentration of crude terephthalic acid in the aqueous slurry, so that non-dissolved crude terephthalic acid will not be supplied to the reactor. Specifically, it has been common that it takes from 0.5 to 3 minutes until the temperature reaches a reaction temperature of from 260° to 320° C. after initiation of the heating of the slurry, and it takes from 3 to 10 minutes to ensure the dissolution, for example, by means of a buffer dissolving vessel after the temperature reaches the reaction temperature prior to the purification by hydrogenation reduction.

As a result of a detailed study by the present inventors, it has been found that when terephthalic acid is exposed to such a high temperature, particularly to a temperature of 250° C. or higher, terephthalic acid undergoes thermal modification, whereby coloring impurities having high molecular weights of from a few hundreds to a few tens thousands will form and that there is a relation such that the shorter the time for exposure to such a high temperature, the smaller the amount of the resulting coloring impurities.

Accordingly, the present invention is characterized in that at the time of dissolving crude terephthalic acid by heating the aqueous slurry of the crude terephthalic acid obtained by oxidation of p-xylene, the time (residence time or retention time) until the purification by hydrogenation reduction is initiated by contacting with a platinum group metal under a hydrogen atmosphere after the slurry is heated to a temperature of 250° C. or higher, is limited within three minutes, preferably within two minutes, so that the time for the exposure to a high temperature is shortened as far as possible to suppress the thermal modification and thereby to suppress formation of coloring impurities.

The lower limit of the time until the initiation of the purification after the temperature reaches 250° C., is not particularly limited, so long as crude terephtharic acid is completely dissolved. However, it is usually at least about 0.5 minutes.

The time until the initiation of the purification after the temperature reaches 250° C., can be made within the above range by controlling the retention time in a buffer dissolving vessel to be short. However, it is preferred to employ a method of shortening the retention time, without using a buffer dissolving vessel, by means of a packed tower type reactor which has, at the upper inlet portion, a retention zone partitioned by an overflow wall and a catalyst-packed layer located below the retention zone, by supplying an aqueous solution of crude terephthalic acid to the retention zone and permitting it to overflow over the overflow wall, so that the aqueous solution of crude terephthalic acid is permitted to flow through the catalyst-packed layer.

This embodiment using a packed tower type reactor having a overflow wall at the upper portion, will be described in detail as follows.

The reactor has a structure in which a retention zone for the aqueous solution of crude terephthalic acid partitioned by an overflow wall, is provided at the upper inlet portion, and a reaction zone having a catalyst-packed layer is provided below the retention zone. The aqueous crude terephthalic acid solution which may contain a certain amount of non-dissolved crystal particles is firstly supplied under pressure to the upper retention zone and permitted to flow from the upper portion of the reactor downward and finally flows out from the bottom of the reactor. Hydrogen is also supplied from the upper portion and dissolved in the liquid phase. In the reactor, a gas phase portion comprising steam and hydrogen gas, is present at the upper portion, and the majority including the entirety of the lower catalyst-packed layer, is a liquid phase portion.

The structure of the above reactor, particularly the structure of the upper portion of the reactor, will be described in further detail with reference to the drawings.

FIG. 1 illustrates the structure of one embodiment of the reactor to be used in the present invention. Reference numeral 1 indicates an inlet for hydrogen, numeral 2 indicates an inlet for the aqueous crude terephthalic acid solution, numeral 3 indicates an overflow wall, numeral 4 indicates a partition plate, numeral 5 indicates a catalyst-packed layer, numeral 6 indicates an outlet for an aqueous terephthalic acid solution, and numeral 7 indicates a flow path of the aqueous terephthalic acid solution. When the reaction is conducted, an interface of the liquid phase and the gas phase is located between the partition plate 4 and the catalyst-packed layer 5. The liquid phase portion is adjusted usually to a height to fill the upper portion of the catalyst-packed layer.

Hydrogen is supplied from the inlet 1 at the top of the tower. Hydrogen is sufficiently dissolved in the aqueous terephthalic acid solution in the high temperature and high pressure tower. However, in order to increase the dissolution efficiency, it is preferred to supply hydrogen gas along the flow path of the aqueous terephthalic acid solution flowing down after the overflow, so that the hydrogen gas is readily taken into the liquid.

The aqueous solution of crude terephthalic acid is supplied from the inlet 2. The inlet 2 is located usually at a height of from 0.2 to 0.4 time of the overflow wall 3 from the partition plate 4, and the portion defined by the overflow wall and the partition plate 4 constitutes the retention zone. Accordingly, the height of the overflow wall 3 is appropriately set taking the retention time of the aqueous solution in the retention zone into consideration. Further, the temperature of the retention zone is set usually at the same level as the reaction zone. The primary significance of this retention zone is to supply the aqueous crude terephthalic acid solution to the reaction zone in a time as short as possible and at the same time to have non-dissolved relatively large crystal particles slightly present in this aqueous solution retained and completely dissolved in the retention zone.

The aqueous solution supplied to the retention zone rises along the overflow wall 3 and finally overflew and is then supplied to the reaction zone below the partition plate 4. Accordingly, even if non-dissolved crystal particles are present, such particles will descend and stay at the lower portion of the retention zone without overflowing and will be subjected to mixing by the currents of the supplied liquid and hydrogen and thereby readily dissolved. The retention of non-dissolved particles depends upon the relation between the rising current of the solution and sedimentation by the action of weight. Accordingly, it is preferred that the speed of the rising current of the solution is adjusted to be relatively small and the capacity of the retention zone is minimized. The retention time in the retention zone varies depending upon the size of the apparatus, but it is usually from 0.5 to 2 minutes.

Accordingly, it is preferred that the cross section in the horizontal direction of the rising portion of the solution be set to be large. For example, in the case of the retention zone in the reactor of FIG. 1, the diameter of the cylindrical portion where the aqueous solution rises and the diameter of the reaction zone are of the same cylinder, and the flow path of the solution flowing down after the overflow, has a cylindrical shape concentric with the inner diameter of the reaction zone. When the inner diameter of the reactor is D, the length of the overflow wall 3 is preferably from 0.3 to 0.9 time of D, and the diameter of the cylindrical portion of the path where the aqueous solution flows down after the overflow, is preferably adjusted within a range of from 0.2 to 0.4 time of D.

Figure 2:
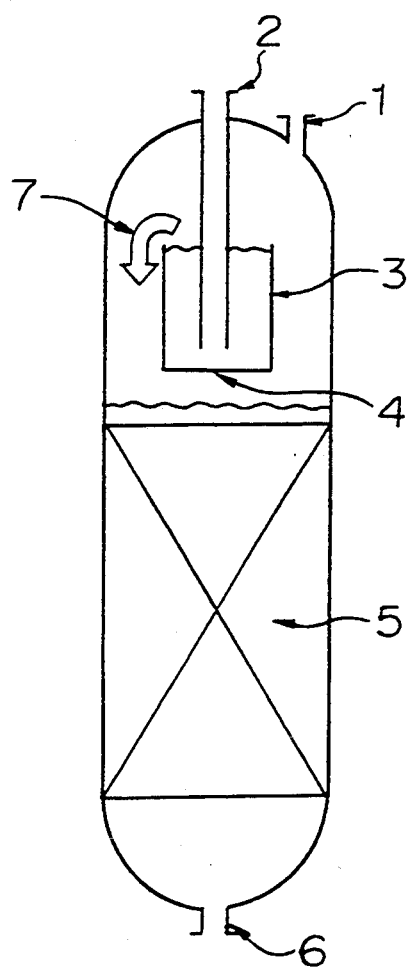
FIG. 2 is a view illustrating the structure of another embodiment of the packed type reactor to be used in the present invention.

So long as the reactor has the structure based on foregoing principle, it may not be limited to the one shown in FIG. 1. For example, the reactor may be the one having a structure as shown in FIG. 2, wherein the aqueous solution of crude terephthalic acid is supplied from an inlet 2 at the top of the reactor, and a reaction zone comprising an overflow wall 3 and a partition plate 4 is provided to enclose the forward end of the inlet 2.

With such a structure, it is possible to prolong the retention time of the non-dissolved crude terephthalic acid crystals having relatively large particle size in the heating line, while shortening the retention time of the rest of the aqueous solution.

Now, the present invention will be described in detail with reference to Examples.

EXAMPLES

In the Examples, the GPC component means coloring impurities in the terephthalic acid product, which have molecular weights of from a few hundreds to a few tens thousands as calculated as standard polystyrene, as determined by the GPC (gel permeation chromatography) analysis.

The amount of the GPC component was represented by the peak area (relative value) of the chromatogram of GPC. Further, the content of 4CBA in the crude terephthalic acid was measured by liquid chromatography. Likewise, the alkali transmittance (hereinafter referred to simply as "T340") was represented by a light transmittance at 340 m$\mu$ as measured by dissolving 7.5 g of crude terephthalic acid in 50 ml of 2N potassium hydroxide and using a quartz cell with a light path length of 1 cm.

Example 1

A hydrogenation test in a fixed bed flow system was conducted by using an apparatus equipped with a vessel for converting crude terephthalic acid to an aqueous slurry, a vessel for measuring the amount, a slurry feed pump, a slurry heating line, a slurry dissolving vessel, a hydrogenation reactor packed with a catalyst having 0.5% by weight of Pd supported on active carbon and a crystallizing vessel. In this apparatus, each equipment and the heating line is provided with an electric heater and a heat insulator as well as a pressure regulator to prevent clogging, and the temperature and the pressure are controlled as accurately as possible.

Firstly, the entire system except for the slurrying vessel was thoroughly flushed with nitrogen gas and pressurized with nitrogen gas to a pressure of 90 kg/cm$^2$G (8.9 MPa). Then, water charged in the measuring vessel, was sequentially circulated by means of the slurry feed pump to the slurry heating line, the buffer dissolving vessel, the reactor and finally to the crystallizing vessel to conduct heating within the system. The heating was adjusted so that the temperature at the final portion of the heating line would reach a reaction temperature of 290° C., and the temperature was adjusted so that in the next buffer dissolving vessel, the temperature would be maintained at 290° C. to ensure the dissolution.

When the temperature was stabilized, a slurry adjusted to contain 2,850 ppm of 4CBA, 30 parts by weight of crude terephthalic acid having a T340 of 38% and 70 parts by weight of water in the slurrying vessel having a capacity of 50 l and equipped with a stirrer, was transferred to the measuring vessel, and feeding (6 l/hr) was initiated by switching from water to the slurry. At that time, the time until the slurry reaches the final portion of the heating line after being heated to 250° C. was 0.5 minute, and the retention time in the dissolving vessel was 1.5 minutes. The slurry was introduced into the reactor, and a hydrogenation reaction was conducted at a hydrogen flow rate of 3 l/hr under a total pressure in the reaction system of 90 kg/cm$^2$G (8.9 MPa) at a reaction temperature of 290° C.

The aqueous terephthalic acid solution treated by the hydrogenation reaction, was continuously sent to the crystallizing vessel, wherein terephthalic acid was crystallized. After separating the mother liquor at a temperature of 100° C., the crystals were washed with water and then dried. The purified terephthalic acid thus obtained was subjected to the GPC analysis, and the results of the GPC analysis are shown in Table 1.

Comparative Example 1

The test was conducted by the same apparatus under the same conditions as in Example 1 except that the retention times in the heating line and the dissolving vessel were changed as shown in Table 1. The results are shown in Table 1.

As is apparent from Table 1, the amount of the GPC component representing coloring impurities increases remarkably as the retention time at a high temperature of at least 250° C. becomes long.

TABLE 1

| | Retention time (minute) | | Amount of the GPC component (Relative value) |
| --- | --- | --- | --- |
| | Heating line | Dissolving vessel | |
| Example 1 | 0.5 | 1.5 | 100 |
| Comparative Example 1 | 0.5 | 5.0 | 272 |

Example 2

This represents an Example wherein the retention time is shortened by using the reactor as shown in FIG. 1.

Starting material crude terephthalic acid (containing 2,700 ppm of 4CBA relative to terephthalic acid) was formed into a slurry having an aqueous solution concentration of 30% by weight. The pressure was raised to 90 kg/cm$^2$G (8.9 MPa), and the temperature was raised to 285° C. by a multitubular heat exchanger. The retention time here was about 90 seconds. The slurry was supplied to the packed tower type reactor of the present invention at a flow rate of 45 m$^3$/hr. The reactor had a structure as shown in FIG. 1, wherein the diameter of the tower was 1,260 mm, a height was 10 m, and the height of the catalyst layer was 7 m. The retention zone had a structure in which the height of the overflow wall was 700 mm, and the diameter of the downflow tube was 300 mm. The retention time here was about one minute. As the reaction conditions, the pressure was 80 kg/cm$^2$G (7.9 MPa), the temperature was 285° C., the flow rate of the hydrogen was 36 Nm$^3$/hr, the catalyst was 0.5% palladium/carbon.

Under such conditions, a continuous operation was conducted for about 170 days, during which there was no trouble of clogging within the reactor, and the obtained purified terephthalic acid had a high quality with the 4CBA concentration being not higher than 6 ppm consistently.

As described in the foregoing, according to the present invention, by specifying the heating conditions before the purification by hydrogenation reduction of an aqueous solution of crude terephthalic acid, it is possible to suppress formation of coloring impurities and to obtain highly pure terephthalic acid having a good color hue.

We claim:

1. A process for producing highly pure terephthalic acid, which comprises heating and dissolving crude terephthalic acid in water, and purifying it by contacting the aqueous solution with hydrogen at a temperature of from 260° to 320° C. in the presence of a platinum group metal catalyst, wherein the hydrogenation is initiated within three minutes after the aqueous solution under heating reaches a temperature of 250° C.

2. The process according to claim 1, wherein the crude terephthalic acid is obtained by an oxidation reaction of p-xylene.

3. The process according to claim 1, wherein the crude terephthalic acid is dissolved in an amount of from 1 to 80 parts by weight per 100 parts by weight of water.

4. The process according to claim 3, wherein the crude terephthalic acid is in an amount of from 15 to 65 parts by weight.

5. The process according to claim 1, wherein the platinum group metal catalyst is palladium supported on active carbon.

6. The process according to claim 1, wherein the hydrogen is supplied by molecular hydrogen in an amount of from 0.05 to 10 $Nm^3$ per 1,000 kg of the aqueous solution of crude terephthalic acid.

7. The process according to claim 6, wherein the amount of the molecular hydrogen is from 0.1 to 3 $Nm^3$ per 1,000 kg of the aqueous solution of crude terephthalic acid.

8. The process according to claim 1, wherein the hydrogenation is initiated within two minutes after the aqueous solution reaches a temperature of 250° C.

9. The process according to claim 1, wherein the total pressure in the reaction system during the hydrogenation by contact with hydrogen is from 5 to 15 MPa.

10. The process according to claim 9, wherein the total pressure is from 6 to 10 MPa.

11. The process according to claim 1, wherein the hydrogenation by contact with hydrogen is conducted by means of a packed tower type reactor.

12. The process according to claim 1, wherein the hydrogenation by contact with hydrogen is conducted by means of a packed tower type reactor which has, at an upper inlet portion, a retention zone partitioned by an overflow wall and a catalyst packed layer located below the retention zone, in such a manner that the aqueous solution of crude terephthalic acid is supplied to the retention zone and permitted to overflow over the overflow wall, and then permitted to flow through the catalyst-packed layer.

13. The process according to claim 1, wherein after the crude terephthalic acid is dissolved in water, the aqueous solution is supplied, without using a buffer dissolving vessel, to a packed tower type reactor which has, at an upper inlet portion, a retention zone partitioned by an overflow wall, and the time until the hydrogenation is initiated after the aqueous solution of crude terephthalic acid reaches a temperature of 250° C., is controlled by adjusting the retention time in the retention zone.

* * * * *